United States Patent [19]
Aulie et al.

[11] Patent Number: 4,792,340
[45] Date of Patent: Dec. 20, 1988

[54] PROSTHETIC ANKLE

[75] Inventors: Alan L. Aulie, Indianola, Wash.;
Ernest M. Burgess, 9 Brook Bay, Mercer Island, Wash. 98040

[73] Assignee: Ernest M. Burgess, Seattle, Wash.

[21] Appl. No.: 78,512

[22] Filed: Jul. 27, 1987

[51] Int. Cl.$^4$ .............................. A61F 2/66; A61F 2/64
[52] U.S. Cl. ........................................ 623/49; 623/21; 403/291; 403/354; 464/78; 464/185
[58] Field of Search ...................... 623/47, 48, 49, 50, 623/52, 53, 55, 21; 464/78, 106, 185; 403/291, 354

[56] References Cited

U.S. PATENT DOCUMENTS 2,937,053  5/1960  Rigney ........................... 403/291
3,700,291 10/1972  Hadland ......................... 403/291
3,940,804  3/1976  Benton et al. .................. 623/47
4,547,913 10/1985  Phillips ........................ 623/53 X
4,645,509  2/1987  Poggi et al. ................... 623/55

Primary Examiner—Richard J. Apley
Assistant Examiner—David J. Bender
Attorney, Agent, or Firm—Seed and Berry

[57] ABSTRACT

A prosthetic ankle having an elongated tubular shank, which provides bending. The shank is part of a monolithic ankle with the lower portion being a flexure joint. The flexure joint has a flexing post defined by an entrapment kerf. The entrapment kerf allows relatively free movement of flexure within defined limits in axial rotation, dorsi and plantar flexion, inversion and eversion. The kerf surfaces provide resistance to axial rotation during dorsiflexion.

7 Claims, 2 Drawing Sheets

PLANTAR FLEXION
.050

NEUTRAL-UNLOADED
.025

DORSIFLEXION BLOCKING
.000

PROSTHETIC ANKLE

BACKGROUND OF THE INVENTION

This invention relates to a prosthetic ankle having controlled limits of motion.

U.S. Pat. No. 4,645,509, entitled Prosthetic Foot Having a Cantilevered Spring Heel, describes a unique prosthetic foot having enhanced flexure characteristics. To provide the best simulation of a natural foot, ankle or leg for amputees, the foot should be attached to a prosthetic ankle that also provides good flexure and controlled limits of movement.

SUMMARY OF THE INVENTION

This invention is a prosthetic ankle that has an an object, the ability to allow flexure of the ankle about three axes of rotation similar to the human natural ankle. The flexure is permitted within prescribed stop limits to prevent excessive motion.

In the preferred ankle, it is an objective to provide flexure, but with resistance to axial rotation when under significant dorsiflexion loads.

It is another object of the invention to provide a prosthetic ankle that is relatively inexpensive to manufacture and has a long fatigue life.

Basically, these objects are obtained by providing an ankle with an elongated flexible shank. The ankle is monolithic and provided with a lower flexure joint. The flexure joint includes an entrapment kerf with the entrapment kerf allowing relatively free movement of flexure about z, y and x axes of rotation, defined respectively as axial rotation, dorsi, and plantar flexion and inversion and eversion. Preferably the kerf provides frictional bearing surfaces under loading causing dorsiflexion which resists heel lateral separation inducing rotation or outer lateral movement of the heels about the axial axis of rotation.

The entrapment kerf provides limits of movement in dorsiflexion and plantar flexion. Preferably the limits are sufficient to allow 5° dorsiflexion and 5° plantar flexion. The kerf controls the limits of dorsiflexion and plantar flexion in an intermediate, double convolute section with the surfaces of the kerf contacting one another to provide the limits of movement.

In the same double convolute section the lateral edges of the kerf provide limits of 5° axial rotation in either direction. Similarly, these same lateral edges provide limits of 3° inversion and 3° eversion.

The surfaces which engage one another to limit dorsiflexion also provide a rubbing friction to resist axial rotation, thus inhibiting the natural tendency for the heels to thrust apart during running or other heavy loading in dorsiflexion.

Since the ankle is monolithic and the flexing area is an intregal part of the flexure joint, the costs of manufacturing are minimized. The shape of the kerf allows ideal limits of movement, so that over flexing of the flexing area is minimized. This will result in a lengthened fatigue life for the flexing area of the ankle.

The shank also provides approximately 3° of flexure to smooth out the torque of dorsiflexion and plantar flexion. The bending or flexing of the shank reduces the shock on the ankle when limits of motion are reached The bending in the shank also is stored as energy which returns in the form of a kick-off to propel the leg forward. The energy stored during bending of the shank provides an assist at toe-off.

DETAILED DESCRIPTION OF THE PREFERRED EMBODIMENTS

Figure 1:
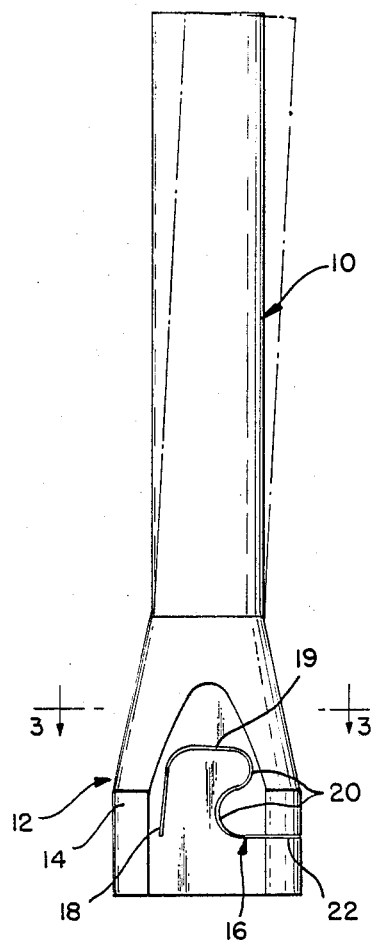
FIG. 1 is a side elevation of the prosthetic ankle made according to the teachings of the invention.
Figure 2:
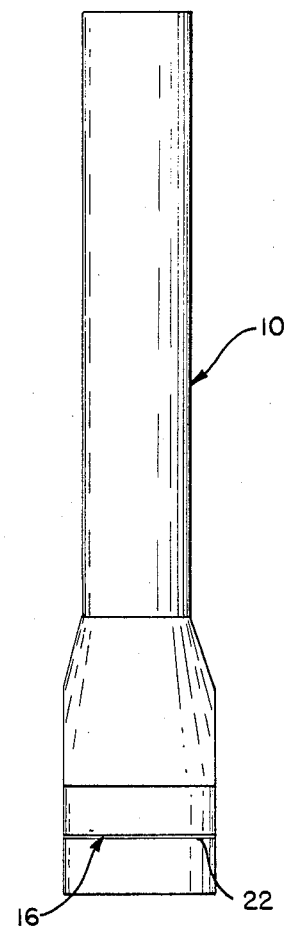
FIG. 2 is a front view of the ankle.
Figure 3:
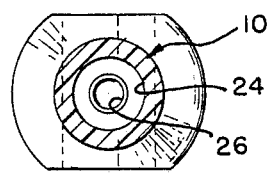
FIG. 3 is a section taken along the line 3—3.
Figure 4:
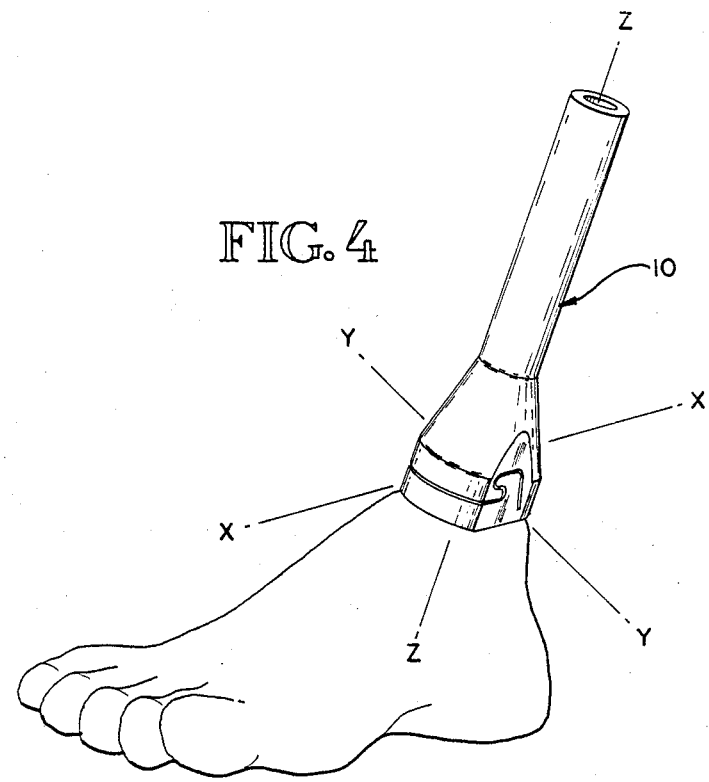
FIG. 4 is an isometric showing the ankle attached to a prosthetic foot.

The prosthetic foot described in U.S. Pat. No. 4,645,509 describes many of the problems of the amputee in trying to get full mobility, including running and jumping with prosthetic devices. The details of that invention are not necessary for an understanding of the prosthetic ankle, however, the details of that description are incorporated herein by reference thereto.

The prosthetic ankle is monolithic, that is, it is of a single piece of polyamide material (preferably nylon). The characteristics of this material are that it is relatively inexpensive, not subject to corrosion, of light weight, noise-free, and requires no maintenance. A material identified as Nylon 6/6, manufactured by polypenco under the designation nylon Polypenco Nylon 101, an unfilled polyamide, extruded round bar of a nominal 2 inches in diameter is the preferred material. The nylon bar, along with the unique kerf, is intended to provide + or −5° axial rotation resisted at a rate of 15 inch pounds per degree of rotation; 3° inversion, 3° eversion resisted at a rate of 20 foot pounds per degree of movement; 5° dorsiflexion of free motion, 5° plantar flexion of free motion, the dorsiflexion is intended to be relatively free followed by dorsiflexion blocking. Additional dorsiflexion beyond the 5° of free rotation is created by the shank bending with the dorsiflexion motion resisted elastically at about 20 foot pounds per degree of flexure. The weight range is approximately 100 grams for 3 inches of the unit to 250 grams for 14 inches of unit. In the manufacturing process, the ankle can be made by the simple machining process of turning on a lathe, boring and then tapping for the insert.

The ankle is provided with an upper shank portion 10 and a lower flexure joint 12. The flexure joint includes a flexing pivot or post 14 defined by the kerf 16. The kerf 16 extends transversely through the full width of the ankle and has a generally vertical rearward portion 18, a generally horizontal intermediate portion 19, a double convolute stop and resistance portion 20, and a forward generally horizontal portion 22.

The ankle is hollow, having an interior bore 24 terminating in a threaded stainless steel insert ⅜-16×0.562 inches manufactured by Heli-Coil Products, a division of Mite Corporation, Danbury, Conneticut, and sold under the trademark "Helicoil." The insert enables the prosthetic foot to be threadably attached to the bottom of the ankle by way of a threaded stud or the like.

Figure 5:
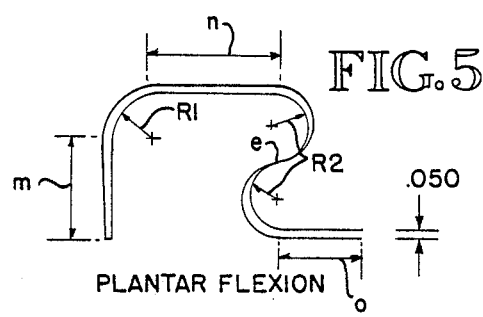
FIGS. 5, 6 and 7 are fragmentary schematics illustrating the stop limits of two examples of motion such as plantar flexion and dorsiflexion.
Figure 6:
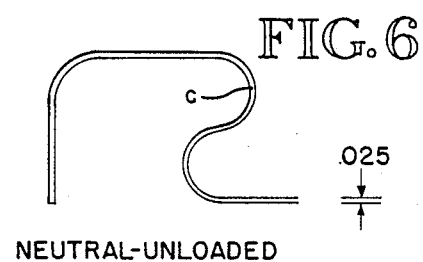
Figure 7:
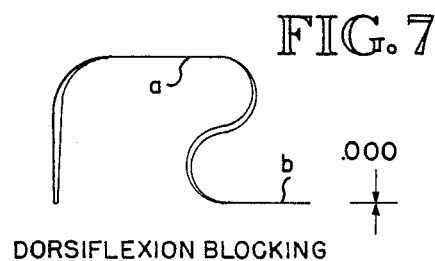

As best shown in FIGS. 5-7, one operation of limit motion is described. FIG. 6 shows the neutral, unloaded condition of the double convolute stop and resistance portion 20. During dorsiflexion, as shown in FIG. 7, the opposed surfaces of the kerf in the double convolute portion will contact limiting the further motion of the flexure joint. Additional motion is absorbed in the shank. Plantar flexion is shown in FIG. 5 with the double convolute surfaces coming together at "e."

The limits of motion are stopped by the surfaces contacting one another at point "b" in dorsiflexion blocking.

Axial rotation is blocked by the kerf coming together at point "c." Eversion and inversion are blocked also at point "a."

As best shown in FIG. 7, during dorsiflexion the surfaces contacting one another at point "b" will be frictionally rubbing one another. Thus, the tendency for the heel to be thrust apart and to cause rotation about axis Z will be resisted by the rubbing contact between the surfaces at point "b.+ The dorsiflexion blocking is perhaps the most important limit provided, in that the lever arm of a foot provides the highest loading and largest bending moments on the ankle. Thus, this dorsiflexion motion is resisted throughout the full transverse surface area of the flexure joint, reducing fatigue in the material. The unique geometry of the kerf, however, allows free flexing within the defined limits defined by the kerf.

The slit is of uniform 0.025 gap. In a preferred ankle the length "m" is 0.550 inches, the radius "R1" is 21/64 inches, the distance between radii "R1" and "R2" identified as "n" is 0.525 inches, radius "R2" is 7/32, distance "o" is 0.625 inches.

While the preferred embodiments of the invention have been illustrated and described, it should be understood that variations will be apparent to one of ordinary skill in the art. Accordingly, the invention is not to be limited to this specific illustration and the drawing.

We claim:

1. A prosthetic ankle providing movement under loading as a prosthetic ankle comprising a monolithic polymeric tubular member having an upper elongated shank portion having an axial centerline and a lower flexure joint, said flexure joint including a rearward pivot post positioned rearwardly of the axial centerline of the shank portion and formed in the shape of an axially short column intended to take high reversing axial loads and an entrapment kerf, the entrapment kerf allowing relatively free movement of flexure about z, y and x axis of rotation, defined respectively as axial rotation, dorsi and plantar flexion, and inversion and eversion, within precise stop limits and providing resistance to axial rotation during dorsiflexion.

2. A prosthetic ankle comprising a monolithic polymeric tubular member having an upper elongated shank portion and a lower flexure joint, said flexure joint including a rearward pivot post and an entrapment kerf, the entrapment kerf allowing relatively free movement of flexure about z, y and x axes of rotation, defined respectively as axial rotation, dorsi and plantar flexion, and inversion and eversion, within precise stop limits and providing resistance to axial rotation during dorsiflexion, said kerf being defined by a generally vertical rearward portion, a generally horizontal, intermediate portion, a double convolute stop and resistance portion, and a generally horizontal forward portion, each portion extending transversely across the width of the flexure joint.

3. The ankle of claim 2, said stop and resistance portion having opposed lateral edges at each convolute that provide positive stops to limit axial rotation in either direction, the stop and resistance portion having opposed surfaces between the convolutes for limiting plantarflexion, said kerf forward portion having opposed surfaces for limiting dorsiflexion.

4. The ankle of claim 3, said kerf forward portion with its opposed surfaces for limiting dorsiflexion during dorsiflexion loading providing friction surfaces when touching during dorsiflexion to resist axial rotational movement caused by the dorsiflexion loading.

5. A prosthetic ankle comprising a monolithic polymeric tubular member having an upper elongated shank portion and a lower flexure joint, said flexure joint including a rearward pivot post and an entrapment kerf, the entrapment kerf allowing relatively free movement of flexure about z, y and x axes of rotation, defined respectively as axial rotation, dorsi and plantar flexion, and inversion and eversion, within precise stop limits and providing resistance to axial rotation during dorsiflexion, wherein the shank is flexible.

6. A prosthetic ankle providing movement under loading as a prosthetic ankle comprising a monolithic polymeric tubular member having an upper elongated shank having an axial centerline and a lower flexure joint, the flexure joint being defined by a rearward flexing post positioned rearwardly of the axial centerline of the shank, formed in the shape of an axially short column intended to take high reversing axial loads and formed by a forward kerf extending across the joint and forward, exiting from the front of the flexure joint, the shank and flexing post providing movement under loading to produce axial rotation, inversion and eversion, and dorsiflexion and plantar flexion, the forward kerf providing freedom of movement but within defined -limit stops.

7. The ankle of claim 6, wherein said kerf provides frictional resistance against heel lateral separation and axial rotation during dorsiflexion.

* * * * *